Figure 1:
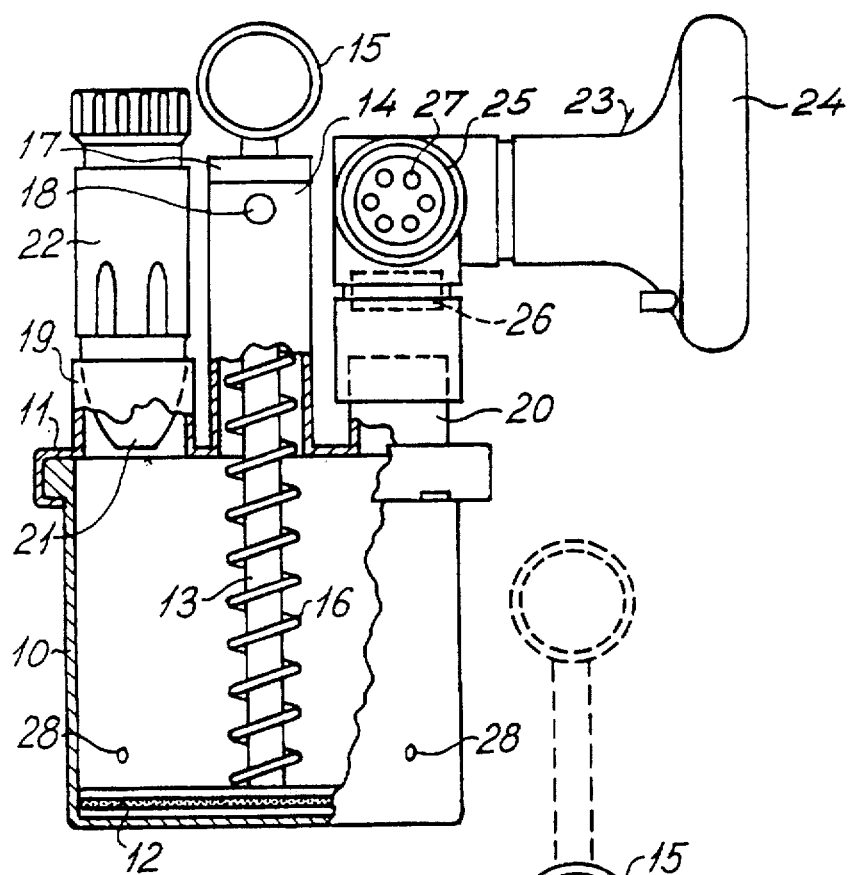

United States Patent [19]

Bisgaard

[11] Patent Number: 5,755,221
[45] Date of Patent: May 26, 1998

[54] AEROSOL INHALER WITH PISTON DUMP

[76] Inventor: Hans Bisgaard, Sollerodvej 80, DK-2840 Holte, Denmark

[21] Appl. No.: 328,967

[22] Filed: Oct. 24, 1994

Related U.S. Application Data

[63] Continuation of Ser. No. 977,394, Apr. 19, 1993, abandoned.

[30] Foreign Application Priority Data

Sep. 12, 1990 [DK] Denmark ............................. 2182/90
Feb. 20, 1991 [DK] Denmark .............................. 297/91

[51] Int. Cl.$^6$ ............... A61M 11/00; A61M 15/00; A61M 16/00; B05D 7/14
[52] U.S. Cl. .................. 128/203.15; 128/200.22; 128/200.23
[58] Field of Search ............... 128/200.14, 200.21, 128/200.22, 203.12, 203.15, 206.26, 203.29, 207.12; 604/54; 222/335; 239/318

[56] References Cited

U.S. PATENT DOCUMENTS

| | | | |
|---|---|---|---|
| 699,255 | 5/1902 | Stevens | 128/200.22 |
| 865,022 | 9/1907 | Dorment | 128/200.22 |
| 905,087 | 11/1908 | Mallory | 128/200.22 |
| 923,822 | 6/1909 | Dorment | 128/200.22 |
| 932,718 | 8/1909 | Rachmann | 128/200.14 |
| 1,693,730 | 12/1928 | Schröder | 128/203.29 |
| 1,998,327 | 4/1935 | McGuire | 128/203.29 |
| 2,115,959 | 5/1938 | Lewis | 128/200.14 |
| 2,141,794 | 12/1938 | King | 128/203.29 |
| 3,658,059 | 4/1972 | Stell . | |
| 3,838,686 | 10/1974 | Szekely . | |
| 3,874,381 | 4/1975 | Baum | 128/200.14 |
| 4,174,052 | 11/1979 | Capra et al. | 222/207 |
| 4,204,539 | 5/1980 | Van Brugge | 128/200.14 |
| 4,300,545 | 11/1981 | Goodnow et al. | 128/200.14 |
| 4,368,850 | 1/1983 | Szekely . | |
| 4,524,769 | 6/1985 | Wetterlin . | |
| 4,598,704 | 7/1986 | Bordoni et al. | 128/203.29 |
| 4,767,416 | 8/1988 | Wolf et al. | 128/200.14 |
| 4,809,692 | 3/1989 | Nowacki et al. | 128/203.29 |
| 4,907,583 | 3/1990 | Wetterlin et al. . | |
| 4,923,448 | 5/1990 | Ennis, III | 128/200.14 |

FOREIGN PATENT DOCUMENTS

| | | | |
|---|---|---|---|
| 0384050 B1 | 12/1992 | European Pat. Off. . | |
| 8102982 | 10/1981 | WIPO . | |
| 9007351 | 7/1990 | WIPO | 128/203.12 |

*Primary Examiner*—Kimberly L. Asher
*Attorney, Agent, or Firm*—Browning Bushman

[57] ABSTRACT

An inhaling device for use in inhaling an active powdered or liquid substance from a reservoir comprising a housing defining a dispersing chamber into which the active substance may be sucked in a dispersed condition, the dispersing chamber being defined by at least one wall part that is movable between first and second positions in which the chamber attains a minimum volume and a maximum volume, respectively, means for biasing the movable wall part toward the second position so as to suck active substance into the dispersing chamber from the reservoir, and a mouthpiece that enables a patient to inhale a dispersed active substance from the dispersing chamber.

29 Claims, 2 Drawing Sheets

AEROSOL INHALER WITH PISTON DUMP

This is a continuation of U.S. application Ser. No. 07/977,394, filed on Apr. 19, 1993, and now abandoned.

BACKGROUND OF THE INVENTION

1. Field of the Invention

The present invention relates to an inhaling device for use in inhaling an active powdered or liquid substance from a reservoir, said device comprising a chamber into which the active substance may be sucked in a dispersed condition, and a mouthpiece by means of which a patient may inhale dispersed active substance form the dispersing chamber.

2. Brief Description of the Prior Art

Various embodiments of inhaling devices or apparatuses of the above type are known. The function of these known devices is conditioned by the creation of an airflow through the inhaling device caused by vigorous inhalation by the patient. This airflow causes active substance to be moved from the reservoir into the airflow in which it is dispersed. Thus, the efficiency of these known devices is to a high degree dependent on the patient's ability to produce a vigorous flow of inhalation air. This means that not only small children, but also adult patients having a lung function that has been weakened for some reason or another, are unable to use these known inhalers or inhaling devices in an efficient manner.

Inhalers, the operation of which is based on the use of a gaseous propellant or a pressurized gas, such as freon, are also known. However, the use of such gaseous propellants often causes unwanted side effect for the patients.

SUMMARY OF THE INVENTION

The present invention provides an inhaling device of the above type by means of which a powdered or liquid active substance may be dispersed efficiently in the air or gas in the dispersing chamber of the device without using special gaseous propellants, even when the patient's lung function is weak or weakened.

The inhaling device according to the invention is characterized in that the dispersing chamber is defined by at least one wall part, which is movable between positions, in which the chamber attains a minimum volume and a maximum volume, respectively, and in moving means for biasing the movable wall part towards the position in which the dispersing chamber attains its maximum volume, so as to suck active substance into the dispersing chamber from the reservoir.

The movable wall part or parts may be moved towards the maximum volume by the moving means with a force or at a rate sufficient to create a suitable vacuum within the dispersing chamber. This causes air to flow from the ambient atmosphere into the dispersing chamber, and the airflow is sufficiently forceful to cause an efficient dispersion of the active substance supplied from the reservoir.

When the active substance has been dispersed in the air within the dispersing chamber, the patient may without any difficulty inhale air and active substance from the dispersing chamber through the mouthpiece, whereby the active substance is inhaled into the patient's lungs.

The reservoir for active substance and the necessary means for moving this substance into the airflow being sucked into the dispersing chamber when moving the movable wall part or parts towards the maximum volume may be inherent parts of the inhaling device according to the invention. Alternatively, the dispersing chamber of the inhaling device according to the invention may be adapted to be connected to another separate inhaler of the type, the operation of which is based on the patient's inhalation ability, for example, as described in Swedish patent specification No. 453,566.

When the patient inhales air and active substance from the dispersing chamber into the lungs, it should be possible to replace the inhaled air by air flowing into the dispersing chamber from the ambient atmosphere. Such a flow of replacement air may, for example, flow into the dispersing chamber through the said separate inhaler. The inhaling device may alternatively or additionally be provided with valve means for communicating the dispersing chamber with the ambient atmosphere immediately before or when said chamber attains its maximum volume. Such valve means may be operated manually, or they may be adapted to open automatically when or immediately before the dispersing chamber attains it maximum volume.

The dispersing chamber may be formed by or comprise a compressible bulb, a collapsible bellows, or a similar pumping device comprising deformable wall parts that form a compressed or collapsed condition may be returned to a distended position under the influence of inherent resilient forces or by means of special elastic returning means. In the preferred embodiment, however, the dispersing chamber comprises a cylinder having a piston arranged therein so as to be displaceable between advanced and retracted positions.

The piston may be connected to a piston rod by means of which the piston may be moved manually between its advanced and retracted positions so that air including dispersed active substance is drawn into the dispersing chamber. In order to obtain a more uniform suction of air into the dispersing chamber and a more uniform dispersion of active substance in such air from time to time, it is convenient, however, to move the piston from its retracted to its advanced position under the influence of a force, which may be kept substantially uniform from time to time and which may be chosen so as to obtain an airflow velocity that is optimum. Thus, the piston may be spring biased towards its advanced position, releasable locking means being adapted to releasably retain the piston in its retracted position. The piston may then manually and against the spring bias be moved to its retracted position, in which the dispersing chamber attains its minimum volume, and the piston may be releasably locked in this position. When the locking means are released, the piston is rather quickly returned to its advanced position under the influence of the spring bias, in which position the dispersing chamber attains its maximum volume. Such piston movement creates a vigorous flow of air towards the dispersing chamber into which airflow active substance is sucked from the reservoir.

At least one through-opening interconnecting the dispersing chamber with the ambient atmosphere may be defined in the wall of the cylinder at a location immediately inside the piston in the advanced position of the piston. In combination with the piston, such openings may function as the valve means described above, because the dispersing chamber is automatically communicated with the atmosphere through such openings immediately prior to the time at which the dispersing chamber attains its maximum volume. When the said openings are passed or uncovered by the piston, air may flow into the cylinder or dispersing chamber through said openings during the very last part of the piston movement because of the vacuum created in the dispersing chamber. Such air inflow creates turbulence within the dispersing chamber, promoting the dispersion of the active substance in the air contained in the dispersing chamber.

As mentioned above, the patient may now inhale dispersed active substance from the dispersing chamber by means of a mouthpiece that may be permanently connected to the dispersing chamber, or that may be mounted thereon when the active substance has been sucked into the dispersing chamber. In order to prevent that the active substance is blown out from the dispersing chamber and wasted if the patient exhales or blows through the mouthpiece, the mouthpiece may communicate with the dispersing chamber through a one-way valve allowing flow of air out from the dispersing chamber only. The mouthpiece preferably communicates with an expiration passage including a one-way valve, allowing air to flow out from the mouthpiece only. The patient may then freely inhale and exhale through the mouthpiece, and air being inhaled then comes from the dispersing chamber, while air being exhaled will flow out through the one-way valve in the expiration chamber.

The reservoir or magazine from which the active substance is released may be adapted to release the active substance in metered standard doses suitable for use by an adult, vide for example the above-mentioned Swedish patent. However, such standard dose is too big when the patient is a child. Therefore, according to the invention the dispersing chamber may comprise an inlet chamber adapted to communicate with the reservoir and a main chamber. The inlet chamber may then be removably connected to the main chamber via a connecting passage, and the mouthpiece may be adapted to be connected to the inlet chamber through the connecting passage, when the inlet chamber is separated from the main chamber. Alternatively, the inlet chamber may be communicating with the main chamber via a one-way valve allowing airflow from the inlet chamber to the main chamber, only. In this case, the mouthpiece may be permanently or removably connected to the inlet chamber. When active substance has been dispersed in the air contained in the dispersing chamber comprising an inlet chamber and a main chamber, the inlet chamber may be removed from the main chamber, if desired, and provided with the mouthpiece if the mouthpiece has not already been arranged on the inlet chamber. The patient may then inhale air and the active substance dispersed therein from the inlet chamber, but not from the main chamber. The volume of the inlet chamber may be chosen so that the amount of active substance, which is dispersed in the air contained in the inlet chamber, is adjusted to the patient in question, who may, for example, be a child. The inlet chamber may possible be designed so that its volume may be adjusted. As an example, the inlet chamber may comprise a cylinder with a piston, which is arranged displaceably therein, and which may be locked in a desired position. In this manner the volume of the inlet chamber may be adapted to the child's age. If the patient is a child who needs an amount of active substance corresponding to half the dose suitable for an adult, the volume of the inlet chamber may be adjusted so that it is substantially equal to the volume of the main chamber.

Alternatively, an inlet chamber with a substantially constant, unchangeable volume may be used. In this case, the inhaling device may comprise two or more inlet chambers having different volumes and/or shapes. It is then possible to select an inlet chamber having a volume suitable for the patient in question.

As an alternative to the use of different inlet chambers or an inlet chamber with an adjustable volume, the stroke of the piston in the cylinder defining the main chamber between its advanced and retracted position may be adjustable. Thus, the piston stroke is increased when the amount of active substance in the inlet chamber is to be reduced.

The inlet chamber may have any suitable shape. As an example, the inlet chamber may be spherical, circularly cylindrical, or have an inner wall defining any other surface of revolution. In such case, where the inlet chamber has a cylindrical wall part, the reservoir is preferably connected to the inlet chamber through a passage, which is directed substantially peripherally in relation to the cylindrical wall part so as to create a whirling airflow pattern therein, promoting dispersion of the active substance.

As mentioned above, the mouthpiece may be permanently connected to the inlet chamber, but the mouthpiece is preferably removably connected to the inlet chamber, so that the same mouthpiece may be used for different inlet chambers. When the inlet chamber has been separated from the main chamber, the section of the connecting passage formed on the inlet chamber may be closed by a suitable lid, and the mouthpiece may then be mounted at another position of the inlet chamber. Alternatively, the said connecting passage section may contain a one-way valve, preventing air from being sucked into the inlet chamber through this connecting passage section.

The mouthpiece may be integral with a unit comprising the expiration passage and the one-way valve arranged therein so that the patient may inhale the air and the dispersed active substance contained in the inlet chamber by inhaling and exhaling or naturally breathing through the mouthpiece.

The spring biasing the piston from its advanced to its retracted position may be so strong that it is difficult or impossible to manually move the piston against the spring bias without using special moving means. As an example, the inhaling device may further comprise a lever device for moving the piston against the spring bias from its advanced to its retracted position.

BRIEF DESCRIPTION OF THE DRAWINGS

The invention will now be further described with reference to the drawings, wherein:

FIG. 1 is a side view and partially sectional view of an embodiment of the inhaling device according to the invention;

FIG. 2 illustrates the same as FIG. 1 immediately after operation of the inhaling device;

FIG. 3 is a perspective view of the inhaling device shown in FIGS. 1 and 2, on which an inlet chamber forming part of the dispersing chamber has been mounted; and FIG. 4 is a perspective view showing the inlet chamber provided with a mouthpiece removed from the main chamber.

DETAILED DESCRIPTION OF THE PREFERRED EMBODIMENTS

The inhaler shown in the drawings comprises a cylindrical container or a cylindrical dispersing chamber 10 closed at the top end by means of a lid 11. A piston 12 (FIGS. 1 and 2) is displaceably arranged within the cylindrical container 10. The piston is connected to a piston rod 13 and movable between an upper position indicated by dotted lines in FIG. 2, and a lower position shown in solid lines in FIGS. 1 and 2. The piston rod 13 extending upwardly through a tubular part 14 formed on the lid 11 is provided with a gripping portion 15, which may be shaped as a ring as shown in the drawings. A coil spring 16 surrounding the piston rod 13 and having its opposite ends engaging with the upper surface of the piston 12 and an upper end wall 17 of the tubular portion 14 is biasing the piston 12 towards its advanced position or bottom position shown in FIG. 1. The piston 12 may be releasably locked in its upper position, which is shown in dotted lines in FIG. 2, by means of a releasable locking member 18. As shown, the locking member 18 may be positioned in the upper part of the tubular portion 14 and be adapted to cooperate with the piston rod 13. As an example, the locking member may be a retaining member that is arranged displaceably in relation to the tubular portion 14 and that may engage with a shoulder or abutment surface formed on the piston rod.

Figure 2:
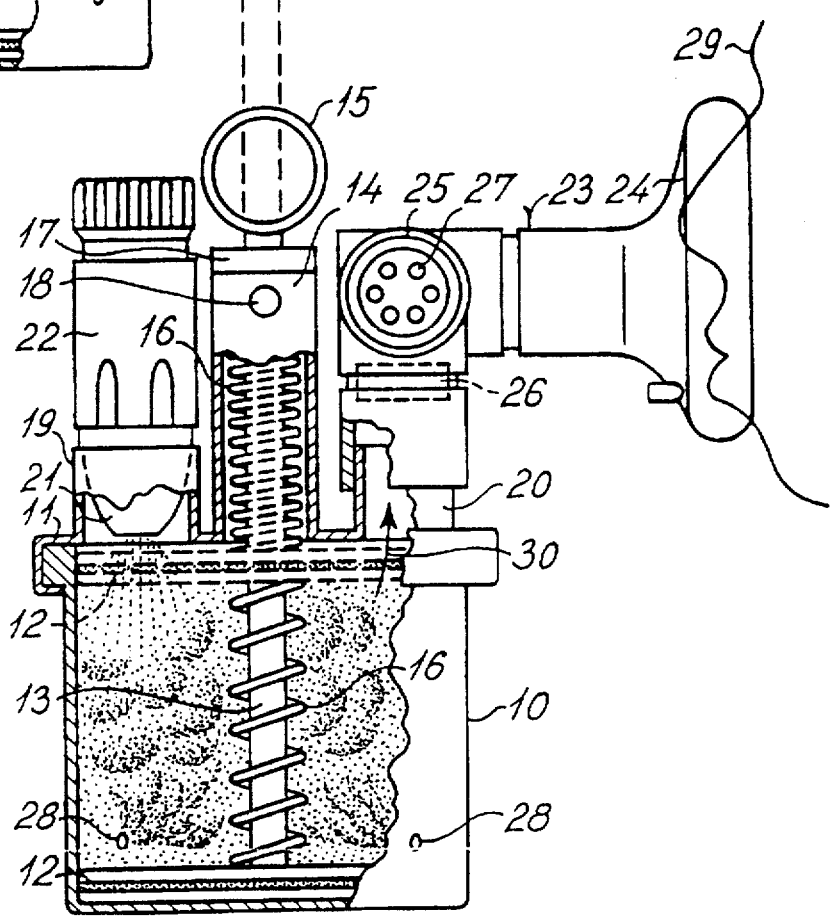

Furthermore, a pair of upwardly directed tube sections 19 and 20, respectively, are formed on the lid 11. As shown in FIGS. 1 and 2, the tube section 19 is adapted to receive a mouthpiece 21 of a conventional inhaler 22, which may, for example, be of the type disclosed in Swedish Patent No. 453,566. A mouthpiece unit 23 comprising a mouthpiece or a mask 24 is removably mounted on the tube section 20. The mouthpiece unit 23 defines an inhalation passage connecting the mask 24 with the inner space of the cylindrical container 10 via the tube section 20. The mouthpiece unit 23 further comprises an expiration branch 25 defining an expiration passage, which is separated from the inhalation passage. The expiration passage contains a one-way valve 26, which may, for example, be a flap valve allowing air to flow through the inhalation passage from the container 10 towards the mask or mouthpiece 24, but prevents airflow in the opposite direction. The expiration passage also contains a one-way valve 27 allowing air to flow out from the expiration passage, while air is prevented from flowing from the ambient atmosphere into and through the expiration passage.

For normal use of the inhaler 22, the mouthpiece 21 is inserted between a patient's lips. Thereafter, the patient inhales vigorously, whereby a standard dose of a powdered inhalation substance is dispersed in the air being caused to flow through the inhaler 22. However, some patients, such as children and adults having a weakened lung function, are not able to inhale sufficiently forcefully to ensure that the inhaler 22 operate at its optimum. This problem may be solved by using the inhaling device shown in FIGS. 1 and 2. The inhaling device may be operated as follows:

The piston 12 may manually be moved to its upper position, indicated in FIG. 2 in dotted lines, by means of the gripping portion 15, whereby the coiled spring 16 is axially compressed. The piston and the piston rod may be locked in this retracted position by means of the locking member 18. When the locking member 18 is released, the piston 12 is moved quickly towards its lower, advanced position, shown in solid lines in FIGS. 1 and 2, under the influence of the bias of the spring 16. Because the removable lid 11 is sealingly connected to an upper rim portion of the container 10, and because the one-way valve 26 prevents air from the ambient atmosphere from being sucked through the mouthpiece unit 23, the sudden downward movement of the piston 12 creates a vacuum within the cylindrical container 10. This vacuum creates a forceful flow of air through the inhaler 22. Consequently, the said standardized dose of inhaling substance is dispersed in the air sucked into the container 10. The cylindrical wall of the container 10 may be provided with one or more through openings 28 at its lower end. Preferably, all of these openings are positioned with substantially the same small spacing from the container bottom. When the piston 12 has passed these openings during its downward movement, air may also flow into the container through these openings 28, whereby increased turbulence is created within the container 10, and such turbulence contributes to an improved dispersion of the powdered inhaling substance in the air contained in the container. The mask 24 may now be placed against a patient's face (FIG. 2) so that it tightly engages the patient's face around the nose and mouth, and the patient may thereafter breath deeply one or several times, whereby air with active substance dispersed therein is sucked into the patient's lungs from the container 10. When the patient is inhaling, air flows from the container 10 through the tube length 20, the inhalation passage of the mouthpiece unit 23 and the one-way valve 26 arranged therein and down into the patient's lungs, as indicated by an arrow 30 in FIG. 2. When the patient is exhaling, air flows from the patient's lungs through the one-way valve 27 and to the ambient atmosphere through the expiration branch 25. The one-way valve 26 prevents, however, that expiration air flows into the container 10. Now, a new standard dose of inhaling substance may be advanced by means of a metering device included in the inhaler 22, and thereafter the inhaling device may again be operated as described above.

The standard dose of inhaling substance suitable for a grown-up patient substantially exceeds the suitable dose, when the patient is a child. The dose of inhaling substance could, of course, be adapted to the child's height or age. However, this would mean that it would be necessary to market a number of different inhalers 22 including different doses. This problem may be solved by means of the inhaling device according to the invention.

Figure 3:
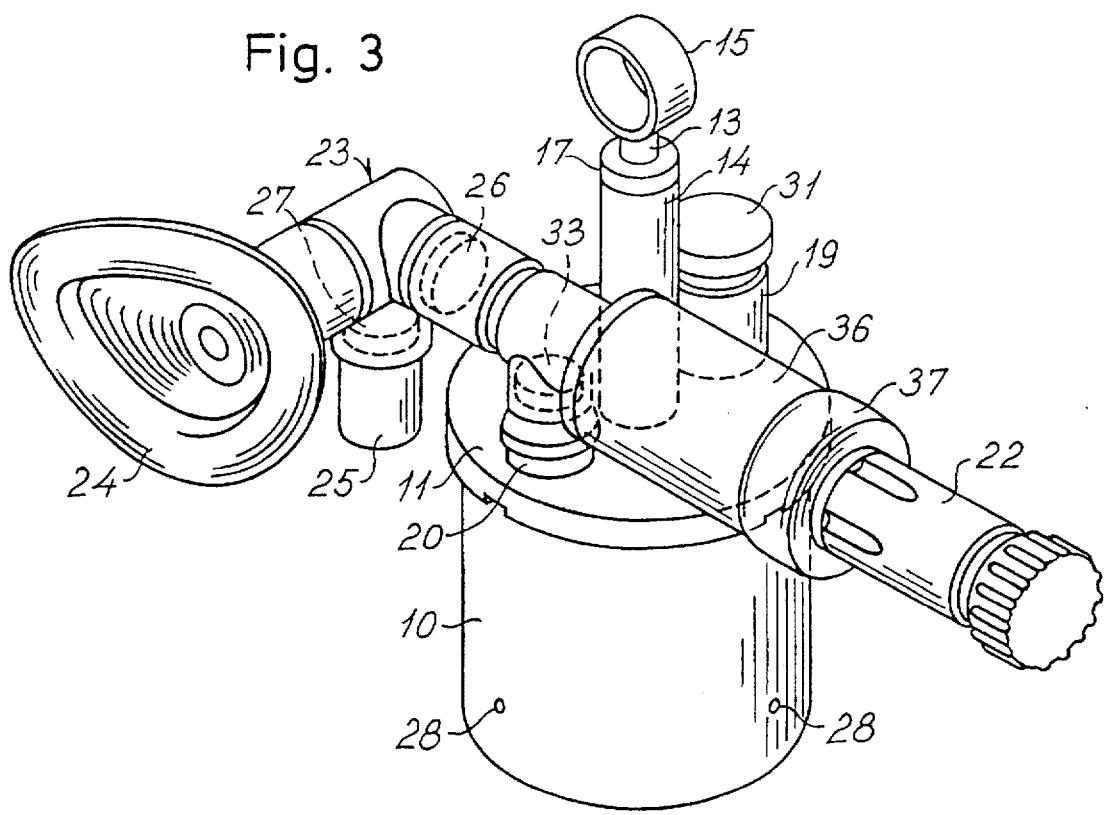
Figure 4:
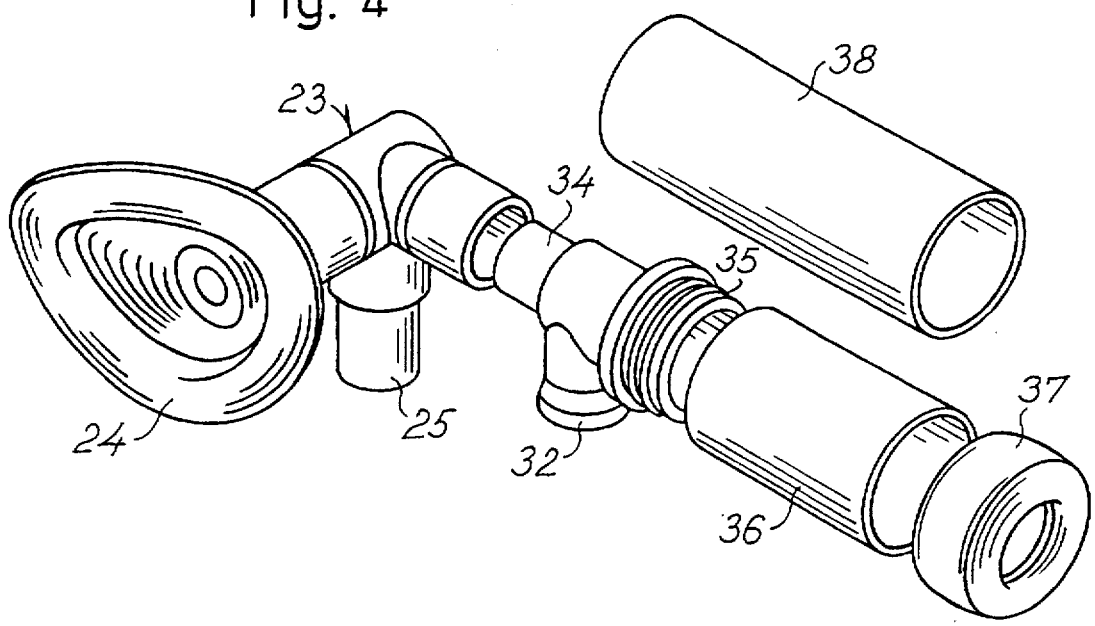

FIG. 3 shows the inhaling device according to FIGS. 1 and 2, where the inhaler 22 has been removed from the tube section 19, which has been closed by means of a lid or stopper 31. The mouthpiece unit 23 has been removed from the tube section 20 and replaced by a T-piece 32 containing a one-way valve 33 allowing air to flow through the free legs or branches of the T-piece and down into the container 10, but not in the opposite direction. The mouthpiece unit 23 is mounted on one branch 34 of the T-piece, while an auxiliary cylinder or an inlet chamber 36 is mounted on the other branch 35 of the T-piece. The inner wall of the cylinder 36 is in sealing contact with the outer surface of the branch 35, which may be provided with peripheral sealing lips or beads. An annular sleeve 37 made from rubber, plastic, or another resilient material may be mounted on the other end of the auxiliary cylinder 36 and defines an opening for sealingly receiving the mouthpiece 21 of the inhaler 22 therein.

The inhaling device shown in FIG. 3 may be operated in a manner similar to that described above. When the piston 12 is moved to its lower advanced position under the influence of the bias of the coil spring 16, the vacuum created within the container 10 causes air to flow through the inhaler 22, and a standardized dose of the inhaling substance is dispersed in said air flow. Thus, air with inhaling substance dispersed therein will fill not only the inlet chamber or auxiliary cylinder 36, but also the cylindrical container or main chamber 10. Now air and inhaling substance contained in the auxiliary cylinder or the inlet chamber 36 may be inhaled by a patient inhaling through the mask 24 in a manner described above. However, the patient cannot inhale air and inhaling substance contained in the main chamber. If desired, the T-piece 32 and the parts mounted thereon may be removed from the tube section 20 before the patient inhales air from the auxiliary cylinder 36. The relationship between the volume of the auxiliary cylinder or inlet chamber 36 and the volume of the main chamber 10 may be chosen so that the patient may inhale a desired fraction of the standardized dose of inhaling substance, which is released by the inhaler 22. The auxiliary cylinder or the inlet chamber 36 may be replaced by another auxiliary cylinder 38 having a volume that is larger or smaller than the volume of the auxiliary cylinder 36, whereby the amount of active substance inhaled by the patient from the auxiliary cylinder or inlet chamber is adapted to the child's age and/or height.

It should be understood that various changes of the embodiment shown in the drawings may be made within the scope of the present invention. As an example, the cylindrical container 10 may be replaced by a bellows or a compressible bulb by means of which a dose of inhaling substance may be sufficiently forcibly sucked from the inhaler 22. It should also be mentioned that the inhaler 22 may be of any type that is adapted to function when the patient is inhaling air therethrough. While the inhaling device according to the invention has especially been disclosed with reference to inhalers for use in connection with powdered inhaling substances, it should be understood that the inhaling device according to the invention may also be used in connection with inhalers operating with liquid inhaling means or substances.

I claim:

1. An inhaling device for use in inhaling an active substance, said device comprising:
    storing means for storing an amount of active substance;
    a housing defining a dispersing chamber therein and having at least one wall part, which is movable between first and second positions in which said dispersing chamber attains a minimum volume and a maximum volume, respectively;
    means for interconnecting the storing means and the dispersing chamber;
    dispersing means for dispersing active substance from the storing means into the dispersing chamber via the interconnecting means and for allowing air to enter said dispersing chamber through one or more air inlet openings;
    resilient biasing means for biasing the movable housing wall part towards its second position, in which the dispersing chamber attains its maximum volume;
    releasable locking means for retaining the movable housing wall part in its first position against the bias of the biasing means, said amount of active substance being dispersed in air sucked into the dispersing chamber when said locking means are released as the dispersing chamber attains its maximum volume, said dispersing chamber attaining its maximum volume in a single actuation;
    a mouthpiece through which a patient may inhale air and active substance dispersed therein from the dispersing chamber; and
    a one-way valve connecting said dispersing chamber to said mouthpiece.

2. An inhaling device according to claim 1, wherein the interconnecting means define a socket for receiving a conventional inhaler therein for communicating with the dispersing chamber.

3. An inhaling device according to claim 1, further comprising valve means for communicating the dispersing chamber with the ambient atmosphere when the movable housing wall part is at least close to its second position.

4. An inhaling device according to claim 1, wherein the movable housing wall part is a piston arranged in the housing so as to be displaceable between advanced and retracted positions.

5. An inhaling device according to claim 4, wherein the piston is spring biased towards its advanced position, the releasable locking means being adapted to releasably retain the piston in its retracted position.

6. An inhaling device according to claim 5, further comprising a lever device for moving the piston against the spring bias from its advanced to its retracted position.

7. An inhaling device according to claim 4, wherein at least one through-opening interconnecting the dispersing chamber with the ambient atmosphere is defined in the wall of the housing at a location immediately inside the piston in the advanced position of the piston.

8. An inhaling device according to claim 1, wherein the dispersing chamber defined in the housing comprises an inlet chamber and a main chamber, the interconnecting means communicating with the inlet chamber, and said at least one movable housing wall part is disposed in said main chamber whereby the main chamber attains a minimum volume and a maximum volume as said movable housing wall part moves from said first to said second position, respectively.

9. An inhaling device according to claim 8, wherein an inlet housing part defining the inlet chamber therein is removably connected to a main housing part defining the main chamber.

10. An inhaling device according to claim 9, and comprising at least two interchangeable inlet housing parts defining inlet chambers having different volumes.

11. An inhaling device according to claim 8, further comprising means for adjusting the volume of the inlet chamber.

12. An inhaling device according to claim 8, wherein the volume of the inlet chamber is substantially constant.

13. An inhaling device according to claim 8, wherein the inlet chamber is defined by a cylindrical wall part with the interconnecting means defining an inlet opening passage, which opening passage is directed substantially peripherally in relation to the cylindrical wall part.

14. An inhaling device according to claim 1, said device comprising:
    a first one-way valve connecting the mouthpiece to the dispersing chamber for preventing air flow into the dispersing chamber through the mouthpiece.

15. An inhaling device according to claim 14, wherein the dispersing chamber defined in the housing comprises an inlet chamber and a main chamber, the interconnecting means communicating with the inlet chamber, and said at least one movable housing wall part being disposed in said main chamber whereby the main chamber attains a minimum volume and a maximum volume as said movable housing wall part moves from said first to said second position, respectively.

16. An inhaling device according to claim 14, wherein the mouthpiece communicates with an expiration passage including a second one-way valve allowing air to flow out only from the mouthpiece.

17. An inhaling device according to claim 16, wherein the inlet chamber communicates with the main chamber via a third one-way valve allowing airflow only from the inlet chamber to the main chamber.

18. An inhaling device according to claim 16, wherein the mouthpiece is integral with a unit comprising the expiration passage in which the second one-way valve is arranged.

19. An inhaling device for use in inhaling an active substance, said device comprising:
    a cylindrical housing;
    a piston defining a substantially closed first chamber in said housing and being movable therein between first and second positions in which the first chamber attains a minimum volume and a maximum volume, respectively, said first chamber attaining its maximum volume in a single actuation;

resilient biasing means for biasing the piston towards its second position, in which the first chamber attains its maximum volume;

means for connecting the closed first chamber with means containing an amount of active substance and defining a substance inlet passage;

releasable locking means for retaining the movable piston in its first position against the bias of the biasing means, the pressure of the first chamber and that of the ambient atmosphere being substantially equalized by a flow of air with said amount of substance dispersed therein being sucked into the first chamber via the substance inlet passage when the locking means are released and the piston is moved from its first to its second position under the bias of the biasing means as said first chamber attains its maximum volume; and a mouthpiece connected through an inhalation passage to said cylinder whereby a patient may inhale air and active substance dispersed therein from the first chamber.

20. An inhaling device according to claim 19, wherein said amount of active substance is contained in a separate inhaler having a suction spout connected to the closed first chamber by the connecting means.

21. An inhaling device according to claim 19, further comprising valve means for communicating the closed first chamber with the ambient atmosphere when the piston is at least close to its second position.

22. An inhaling device according to claim 19, wherein at least one through-opening interconnecting the closed first chamber with the ambient atmosphere is defined in the wall of the cylindrical housing at a location immediately inside the piston when the piston is in its second position.

23. An inhaling device according to claim 19, wherein the mouthpiece communicates with the closed first chamber via a first one-way valve in said inhalation passage, allowing flow of air out from the closed first chamber only.

24. An inhaling device according to claim 23, wherein the mouthpiece communicates with an expiration passage including a second one-way valve allowing air to flow out only from the mouthpiece.

25. An inhaling device according to claim 19, wherein the connecting means defines a second chamber communicating with the first chamber.

26. An inhaling device according to claim 25, wherein the second chamber communicates with the first chamber via a third one-way valve allowing airflow only from the second chamber to the first chamber.

27. An inhaling device according to claim 25, wherein an inlet housing part defining the second chamber therein is removably connected to the cylindrical housing defining the first chamber.

28. An inhaling device according to claim 25, further comprising means for adjusting the volume of the second chamber.

29. An inhaling device according to claim 19, further comprising a lever device for moving the piston against the bias from the biasing means from the second to the first position.

* * * * *